United States Patent [19]

Brewster

[11] 4,192,757

[45] Mar. 11, 1980

[54] ALKYL PHENOL SOLUTIONS OF ORGANO MOLYBDENUM COMPLEXES AS FRICTION REDUCING ANTIWEAR ADDITIVES

[75] Inventor: Philip W. Brewster, Camlachie, Canada

[73] Assignee: Exxon Research & Engineering Company, Florham Park, N.J.

[21] Appl. No.: 898,769

[22] Filed: Apr. 21, 1978

[51] Int. Cl.$^2$ .................. C10M 1/38; C10M 1/48; C10M 1/54
[52] U.S. Cl. .................. 252/32.7 E; 44/68; 252/42.7; 252/49.7; 260/429 D; 260/429 R
[58] Field of Search .................. 252/42.7, 32.7 E; 260/429 D, 429 R; 44/68

[56] References Cited

U.S. PATENT DOCUMENTS

| | | | |
|---|---|---|---|
| 2,270,183 | 1/1942 | Cook | 252/42.7 |
| 3,047,500 | 7/1962 | Matson | 252/42.7 |
| 3,184,410 | 5/1965 | Bretherick | 252/42.7 |
| 3,356,702 | 12/1967 | Farmer et al. | 252/42.7 |
| 3,541,014 | 11/1970 | Le Suer | 252/42.7 |
| 3,636,023 | 1/1972 | Murray et al. | 260/429 D |
| 4,011,167 | 3/1977 | Chibnik | 252/42.7 |
| 4,121,025 | 10/1978 | Scott | 260/45.75 R |

FOREIGN PATENT DOCUMENTS 882295 11/1961 United Kingdom .

Primary Examiner—Arthur P. Demers
Attorney, Agent, or Firm—Roland A. Dexter

[57] ABSTRACT

A solution of a hydrocarbon-soluble organo molybdenum complex obtained as the solution reaction product of a hydrocarbyl substituted thio-bis-phenol, e.g. 2,2$^1$-thio-bis(4-iso-nonyl phenol), with a molybdenum compound, e.g. molybdic oxide, in the presence of an amine, e.g. ethylene diamine, in a solvent of a $C_8$–$C_{50}$ alkyl substituted phenol, e.g. nonyl phenol, is a useful hydrocarbon additive, particularly when used in combination with an oil-soluble sulfur donor, e.g. a metal dialkyl dithio phosphate, which provides an additive combination for lubricants and fuels whereby the resulting lubricating composition exhibits an improved antifriction property.

15 Claims, No Drawings

ALKYL PHENOL SOLUTIONS OF ORGANO MOLYBDENUM COMPLEXES AS FRICTION REDUCING ANTIWEAR ADDITIVES

BACKGROUND OF THE INVENTION

The present invention relates to alkyl phenol solutions of hydrocarbon-soluble molybdenum complexes of thio-bis-phenols, their method of preparation and their utility as an additive for hydrocarbon compositions such as gasoline, fuel oil and lubricating oils including greases, industrial oils, gear oils and lubricants for engines and other equipment having moving parts operating under boundary lubricating conditions.

There are many instances, as is well known, particularly under "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known additives which may be classified as antiwear, antifriction and extreme pressure agents and some may in fact satisfy more than one of these functions as well as provide other useful functions, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates are one of the additives which are known to exhibit antioxidant and antiwear properties. The most commonly used additives of this class are the zinc dialkyl dithiophosphates which are conventionally used in lubricant compositions. While such zinc compounds afford excellent oxidation resistances and exhibit superior antiwear properties, it has heretofore been believed that the same increases or significantly limits the ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction, e.g. in crankcase motor oils include the use of synthetic ester base oils which are expensive and the use of insoluble molybdenum sulfides which have the disadvantage of giving the oil composition a black or hazy appearance.

Other types of molybdenum compounds taught to be useful in lubricating oils include the alkyl esters of molybdic acid as corrosion inhibitors (see U.S. Pat. No. 2,805,997) and nitrogenous thiomolybdates as metal antiwear additives which are said to function by providing a coating of reduced coefficient of friction (see U.S. Pat. No. 2,938,869).

Similarly, antifriction agents or oiliness or lubricity agents as the same are often referred to in the prior art, function by forming a coating on the surface of the moving metal parts. As in the case of antiwear agents, however, the coating bonds are, generally, effected physically, rather than chemically, and, indeed, the bonding between an antifriction agent and the surface is, generally, weaker than the bond formed between an antiwear agent and the metal surface.

In light of the foregoing, the need for improved lubricating compositions that will permit operation of moving parts under boundary conditions with reduced friction is believed to be readily apparent. Similarly, the need for such a composition that can include conventional base oils and other conventional additives such as ashless dispersants, detergents, antioxidants (e.g. 2,6-di-tert. butyl para-cresol, methylene bis(4,4'-di[2,6-di-(tert. butyl) phenol]-see U.S. Pat. No. 3,591,497, col. 2, lines 49–52), V.I. improvers, etc., and can be used without the loss of other desirable lubricant properties, particularly those provided by zinc dialkyl dithiophosphates, is also readily apparent.

SUMMARY OF THE INVENTION

In U.S. patent application Ser. No. 843,964 filed Oct. 20, 1977, and of common assignee to this application, there is a teaching of a class of organo molybdenum complexes believed to be represented by the following formula I:

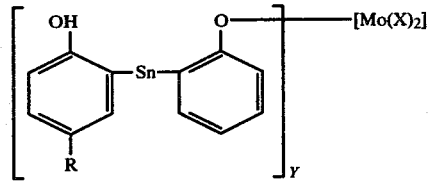

where n is 1–3, Y is 1–2, X is selected from sulphur or oxygen and R is a substantially hydrocarbyl group containing from 1 to 50, preferably 12 to 28, carbon atoms and X is selected from sulphur or oxygen. These complexes are produced by the solution reaction of a thio-bis-phenol, a source of molybdenum and an amine in a mineral oil solvent which are reported therein as useful friction-reducing additives for lubricants and fuels. It has now been discovered that said complexes containing from about 0.5 to about 5, preferably 1 to 2.5, optimally 1.4, wt.% nitrogen are more readily produced in quantitative yields at lower temperatures and with a broader spectrum of amines (all with respect to said teaching) when their preparative reaction is carried out in an alkyl phenol solvent wherein said phenol is a $C_5$ to $C_{50}$, preferably $C_8$ to $C_{18}$, optimally $C_{9(ave.)}$ alkyl substituted phenol.

The amine reactants include ammonia, simple amines such as $C_6$–$C_{30}$ alkyl amines, alkylene polyamines such as ethylene diamine (preferred) and diethylene triamine, alkanolamines such as ethanolamine, ethoxylated derivatives of alkylene diamines such as hydroxyethyl ethylene diamine, urea and ureides. When said complex is introduced into the lubricating oil in combination with said phenol, e.g. as the solution of said reaction, the modified lubricating oil exhibits a dynamic coefficient of friction comparable to if not somewhat better than that result obtained with the addition of only a common amount of organo molybdenum complex.

In accordance with the present invention, the foregoing and other objects and advantages are accomplished with a hydrocarbon composition comprising a major proportion of a hydrocarbon, e.g. a lubricating oil, and at least a friction reducing amount of a solution said organo molybdenum complex in $C_8$–$C_{50}$ alkyl phenol and preferably a lubricity enhancing combination of: (a) said organo molybdenum complex; (b) said $C_5$ to $C_{50}$ alkyl phenol and (c) an oil-soluble sulfur donor, preferably zinc dialkyl dithiophosphate, and, if desired, at least a sludge-dispersing amount of an oil-soluble dispersant, e.g. an ashless dispersant, and at least a rust-inhibiting amount of a rust inhibitor. In practice, the lubricity enhancing combination is present in an amount sufficient to provide from about 0.005 to 0.2, preferably 0.03 to 0.15, optimally about 0.1, wt.% molybdenum, at least about 0.25, e.g. 0.25 to 1, wt.% sulfur donor and from 0.25 to 5 wt.% $C_8$–$C_{50}$ alkyl phenol, all weight percent being based on the total weight of the hydrocarbon composition such as lubricating oil or fuel.

DETAILED DESCRIPTION OF THE INVENTION

Oil-Soluble Organo Molybdenum Compound

The hydrocarbon-soluble molybdenum complexes are believed to be derived from a thio-bis-phenol as shown in Formula I. The R group of said Formula I as defined is substantially hydrocarbyl and thus is alkyl, aryl, aralkyl, cycloalkyl, or alkaryl; however, the hydrocarbyl group may contain polar substituents such as amino, aminoalkyl, hydroxy, hydroxyalkyl, halo, mercapto, keto, phosphinyl, phosphoryl, thiophosphoryl and dithiophosphoryl radicals.

Specific examples of the R group includes methyl, ethyl, propyl, isopropyl, isobutyl, n-butyl, sec-butyl, tert-butyl, n-hexyl, heptyl, octyl, nonyl-decyl, dodecyl, tridecyl, heptadecyl, octadecyl, polyisobutyl and polypropyl.

The organic molybdenum complexes are the reaction product of a thio-bis-phenol, an amine and molybdenum. The aforesaid thio-bis-phenols can be characterized by Formula II:

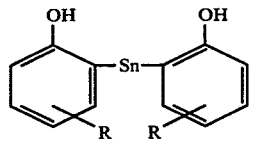

II wherein R and n are each the same as previously described with R preferably para to the hydroxyl substituent. These thio-bis-phenols are readily produced from the reaction of alkyl phenols and a source of sulfur, e.g. chemical sulfur or sulfur halides. The alkyl phenols are readily produced by the reaction of an alpha-olefin or mixtures thereof, e.g. a nonene-1 cut which is primarily $C_9$ but including some $C_8$ and $C_{10}$ olefins as well, with phenol in the presence of an alkylation catalyst e.g. $BF_3$ whereby a reaction product mixture of primarily monoalkyl phenols (most para to the hydroxyl group) but with a minor amount, e.g. 20–35 wt.%, of di-(alkyl) phenols and a small amount, e.g. 2 to 5 wt.%, of tri-(alkyl) phenols is obtained.

A particularly useful reactant for the preparation of the molybdenum complex can be characterized by Formula III.

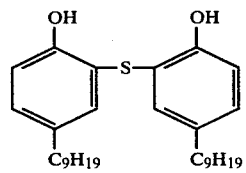

III

The source of molybdenum is a molybdenum containing compound capable of reacting with the thio-bis-phenol to provide a molybdenum complex containing from about 0.5 to 20, preferably 2 to 10, optimally about 5 wt.% molybdenum based on the total weight of said complex. The sources of molybdenum include molybdic trioxide also known as molybdic anhydride, ammonium thiomolybdate, ammonium bismolybdate, molybdenum halides, and ammonium heptamolybdate tetrahydrate.

The organo molybdenum complex is substantially the product of a solution reaction between 1–2 moles thio-bis-phenol, 1 mole of molybdenum and 1–2 moles of an amine. The reaction is readily carried out by reaction at an elevated temperature of from 135° C. to 225° C., preferably 160° C. to 190° C., optimally 175° C. to accelerate said reaction and remove the water of reaction. The reaction is carried out in a $C_8$ to $C_{50}$, preferably $C_8$ to $C_{18}$, alkyl substituted phenol, optimally $C_{9(average)}$ alkyl phenol. The reaction is carried out over a period of from about 4 to 20, preferably 6 to 12, hours in order to suitably stabilize the complex and for removal of the water of reaction as by nitrogen sparging or distillation at atmospheric or reduced pressure.

Amines

The amine reactants broadly contain from 1 to 5, preferably 2, nitrogens and from 0 to 60, preferably 2 to 20 carbons. The preferred amines are of the class consisting of: $C_6$–$C_{30}$ alkyl amines such as n-octyl amine and dodecyl amine; alkylene polyamines which can be represented by the general formula $NH_2(CH_2)_n$—$[NH(CH_2)_n]_m$—$NH_2$ wherein n is 2 to 3 and m is a number from 0 to 3 including ethylene diamine, diethylene triamine, tetraethylene pentamine and mixtures of such polyamines formed from the reaction of ethylene dichloride and ammonia or ethylene imine and ammonia; alkanolamines such as ethanolamine and diethanolamine; ethoxylated derivatives of alkylene polyamine such as hydroxyethyl ethylene diamine and the reaction product of alkylene oxides such as an ethylene oxide or propylene oxide with polyamines e.g. dinitrilo tetraethanol; urea and ureides such as ethylurea.

Carrying out the organo molybdenum complexing reaction in a $C_5$–$C_{50}$, preferably $C_8$–$C_{18}$, optimally $C_9$, alkyl phenol solvent in an amount ranging from about 0.25 to 5, preferably 1, parts by weight of phenol per part by weight of organo molybdenum complex product provides a number of benefits over a reaction without solvent or in a light aromatic solvent such as toluene or a light hydrocarbon oil, e.g. mineral oil including: a faster reaction time; completion of reaction to a stabilized molybdenum complex at a lower temperature; faster and simpler filtration of the reaction product solution; and, a product solution which when added to lubricating oil provides comparable if not enhanced friction reduction (as seen from the subsequent Table I).

Alkyl Phenols

The $C_5$ to $C_{50}$, preferably $C_8$–$C_{18}$, alkyl phenols useful as solvents for the organo molybdenum complexing reaction are generally the same as the alkyl phenols described to be reactive with a source of sulfur to provide the thio-bis-phenols of Formula I Rather than broadly covering $C_1$ to $C_{50}$ alkyl phenols the solvent class is broadly limited to $C_5$ to $C_{50}$ alkyl phenols. Their method of preparation is the same as earlier described and as a class generally commercially available. Described herein as the optimum alkyl phenol is a $C_8$–$C_{10}$, i.e. $C_{9(average)}$ alkyl substituted phenol commercially available as ECA 9003 from Exxon Chemical Company of Houston, Texas. Broadly, amyl phenol through pentacontanyl phenol are useful with octyl phenol through octadecyl phenol being preferred.

The $C_5$–$C_{50}$ alkyl phenols are usefully present in the hydrocarbon composition in an amount of from about 0.25 to 5, preferably 1, parts by weight per part by weight of the organo molybdenum complex.

Sulfur Donors

The $C_8$–$C_{50}$ alkyl phenol solutions of the hydrocarbon-soluble organo molybdenum complexes provide enhanced lubricity in lubricating oils when used in combination with an active sulfur donor which can be defined as a compound which when used in admixture with the organo molybdenum complex reduces the coefficient of friction at least about 10% relative to that provided by the complex alone. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

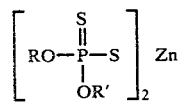

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl, n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid will average about 5 or greater.

The zinc dihydrocarbyl dithiophosphates which are useful as a coadditive, i.e. sulfur donor of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier, an equally suitable active sulfur donor is the dihydrocarbyl esters of dithiophosphoric acid which may be represented by the formula:

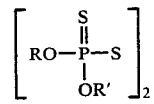

where R and R' are as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2$–$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

Other Additives For Lubricating Compositions

In addition to the organo molybdenum complex alkyl phenol and active sulfur donor, a lubricating oil composition may contain other well-known lubricating oil additives to provide trouble-free operation of the lubricated equipment, such as ashless dispersants, metallic detergents, supplemental oxidation and corrosion inhibitors, extreme pressure agents, rust inhibitors, pour point depressants, viscosity index improvers, etc.

1. Ashless Dispersants

As used herein, the terminology "ashless dispersant" is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1, e.g. 1 mole of $C_{70}$–$C_{100}$ polyisobutenyl succinic anhydride to 2 moles of tetraethylene pentamine.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

$NH_2(CH_2)_n$—$[NH(CH_2)_n]_m$—$NH_2$ wherein n is 2 to 3 and m is a number from 0 to 10. Specific compounds coming within the formula include diethylene triamine, tetraethylene pentamine, dipropylenetriamine, octaethylenenonamine, and tetrapropylenepentamine; N,N-di-(2-aminoethyl)ethylenediamine may also be used. Other aliphatic polyamino compounds that may be used are N-amino-alkylpiperazines, e.g. N-(2-aminoethyl)piperazine. Mixtures of alkylene polyamines approximating tetraethylene pentamine are commercially available, e.g. Dow E-100 sold by Dow Chemical Company of Midland, Mich.

Representative dispersants are formed by reacting about one molar amount of polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric acid to the reaction mixture after the imidation or esterification is substantially complete and heating the mixture at temperatures of 100° to 150° C. for a few hours.

2. Other Additives

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert butyl para-cresol amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrollidone or dimethylaminoalkyl methacrylate, post-grafted polymers of ethylene-propylene with an active monomer such as maleic anhydride which may be further reacted with an alcohol or an alkylene polyamine, styrene/maleic anhydride polymers post-reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the additive combination of oil-soluble organo molybdenum complex $C_5$–$C_{50}$ alkyl phenol and active sulfur donor are used as an additive concentrate, the concentrate may consist essentially of from about 5 to 95% of the additive combination, the remainder being an additional hydrocarbon solvent such as kerosene, mineral oil, a naphtha and the like or a $C_5$–$C_{50}$ alkanol as disclosed in my copending application (Ser. No. 898,839) filed on Apr. 21, 1978. The preferred concentrate contains about 40 to 90% of the additive combination in a second solvent of mineral oil.

Whether the organo molybdenum complex-alkyl phenol solution is used alone or in combination with an active sulfur donor, its concentration may vary appreciably with the particular hydrocarbon. For example, when said molybdenum complex-alkyl phenol solution is used alone in a fuel such as gasoline, the concentration of the complex ranges from 10 to 1,000, preferably 20 to 50 weight parts per million based on the total weight of the fuel composition, whereas in a lubricant, it is used in combination with the active sulfur donor, which three-component combination then ranges from about 0.5 to 5, preferably 1 to 3 wt.% based on the total weight of the lubricating oil.

The invention will be further understood by reference to the following examples which illustrate a preferred form of the invention and compares the same with different, though similar compositions.

The following examples illustrate more clearly the compositions of the present invention. However, these illustrations are not to be interpreted as specific limitations on this invention.

EXAMPLE 1

Nonyl phenol sulfide (183 g) as ECA 9001, Solvent Neutral 150 mineral oil (183 g) and molybdic trioxide (28.1 g) as an undensified grade obtained from Climax Molybdenum Company, Fort Madison, Wis. were stirred together and then raised in temperature to 94° C. at which time ethylene diamine (23.4 g) was thereafter slowly added over a 20-minute period. The temperature was raised with stirring to 121° C. over 0.6 hour. While stirring at this temperature, the volatiles including water and ammonia were removed by gentle nitrogen sparging for 18 hours. After filtration, the resulting product solution, useful as a lubricating oil additive, had a viscosity of 177 S.U.S. @ 100° C. and was black in color and contained about 4.3 wt.% molybdenum and 1.9 wt.% nitrogen. ECA 9001, a 70 wt.% active mineral solution of di-(C9 average) nonyl phenol sulfide is commercially available from Exxon Chemical Company, Houston, Tex.

This is an organo metallic complex prepared according to the teachings of said copending Application Ser. No. 843,964 using a mineral oil solvent for the reaction medium. Filtration through a steam-heated Buchner funnel holding a ¼ precoat of Celite 535 took in excess of one hour. Exposure of the product solution to about 150° C. for 3 hours reduced its nitrogen content to 1.43 wt.% and appeared to evolve ammonia during said 3 hours.

EXAMPLE 2

The procedure of Example 1 was followed except that the mineral oil was replaced by: 183 g of nonyl phenol (as ECA 9003, a C9 average) nonyl phenol containing about 62 wt.% monoalkyl and 33 wt.% dialkyl phenol; use of densified $MoO_3$; going to 177° C. over a 2-hour period while adding the ethylene diamine; and reacting at 177° C. for 4 hours prior to filtration. The resulting filtered product solution (the filtration of which took less than 10 seconds to fully filter) analyzed for 4.5 wt.% molybdenum.

EXAMPLE 3

As earlier noted before, a preferred process provides for from 6 to 12 hours exposure of the reaction medium to a temperature of about 175° C., usefully 160° C. to 190° C. This is shown in a procedure in which 183 weight parts of nonyl phenol sulfide (e.g. ECA 9001) are admixed with 183 weight parts of nonyl phenol (e.g. ECA 9003) and heated toward 105° C. during which time 28.1 weight parts of molybdic trioxide are added. When 105° C. is reached 23.4 weight parts of ethylene diamine is slowly added over a 30-minute period. Thereafter raise the temperature to about 150° C. and initiate inert gas (e.g. nitrogen) sparge. Raise to about 175° C. during the next 2-hour period and heat soak at 175° C. for about 4 to 6 hours after which it can be readily filtered as shown in Example 2.

EXAMPLE 4

A lubricating oil composition was prepared for comparative testing of additives by blending together the individual components, noted below, usually at a slightly elevated temperature, i.e. from about 45° C. to above 65° C. to insure complete mixing. The final composition of Blend 4 formulated into a 10W/30SE quality automotive engine oil was as follows:

| Blend 4 | |
|---|---|
| Wt. % Active Ingredient | |
| Mineral Oil | 94.9 |
| Ashless Dispersant | 2.9 |
| Magnesium Sulfonate | 0.2 |
| ZDDP[(1)] | 0.9 |
| Rust-Inhibitor | 0.1 |
| Viscosity Index Improvers | 1.0 |

| -continued | |
|---|---|
| Blend 4 | |
| Wt. % Active Ingredient | |
| Silicone Defoamer | 0.01 |
| Ashless Antioxidant | — |
| Metal Detergent-Inhibitor | — |

[(1)]Zinc dihydrocarbyl dithiophosphate such as zinc dinonyl phenol dithiophosphate This formulated blend was itself and in modified forms according to the teaching of this invention and the teaching of said Ser. No. 843,964 subjected to testing as hereinafter set forth:

1. Testing Procedure A

The Roxana Four-ball wear tester with the Brown/GE modification from Roxana Machine Works, St. Louis, Mo. was used to measure friction properties by the following procedure. The tester was assembled in the normal wear procedure as described in ASTM D2266-67 using four ½" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 110° C. and 15 kg for 15 minutes or until frictional force has stabilized.

The compounds of the invention were then evaluated by subjecting the products to a study of their utility as a lubricity enhancing and/or antiwear additive for lubricating oils by using the Testing Procedure A. The weight percentage of amounts of molybdenum complex added is given in amount of complex added.

The results of tests under Procedure A are set forth in Table I.

From Table I, it is shown that the additive combination of the invention provides improved lubricity enhancement to lubricating oils when an active sulfor donor is present and that these combinations have utility as additives for lubricating oils.

While the additive combination of this invention provides frictional performance to a fully formulated lubricating oil comparable to that provided by an additive according to the teaching of said application Ser. No. 843,964, it is much easier to filter and thereby remove unwanted and deleterious reaction by-products than the product-hydrocarbon solutions prepared according to the teachings of said Ser. No. 843,964, e.g. where a quantity of the former as shown by Example 2 filters through in about 10 seconds a similar quantity of the latter would take from 0.5 to several hours (see Example 1 where it took in excess of 1 hour). In this regard, a solvent mixture of up to an equal amount of mineral oil with said alkylphenol solvent provides slower but still useful filtering periods of the solution reaction products.

Another advantage of said alkyl phenol as a solvent for the reaction of the hydrocarbyl phenol sulfide and molybdenum compound, preferably molybdic oxide ($MoO_3$), resides in the enhanced reactivity of the components, i.e. shorter reaction times and/or more heat stable complexes when such a solvent is used as compared with mineral oil solvent.

It is to be understood that the Examples present in the foregoing specification are merely illustrative of this invention and are not intended to limit it in any manner; nor is the invention to be limited by any theory regard-

TABLE I

| Test | Added Mo Complex Solution of Example # | Wt (%) | Coefficient of Friction 46 cm/sec | 1 cm/sec | Friction Reduction (%) 46 cm/sec | 1 cm/sec |
|---|---|---|---|---|---|---|
| 1 | — | — | 0.084 | 0.101 | — | — |
| 2 | 1 | 2.2 | 0.044 | 0.056 | 47.6 | 44.6 |
| 3 | 2 | 2.2 | 0.040 | 0.061 | 52.4 | 39.6 |

What is claimed is:

1. In a concentrate consisting essentially of one part by weight of an organo molybdenum complex obtained from a solution reaction of 1-2 moles of a $C_1$ to $C_{50}$ hydrocarbyl substituted thio-bis-phenol, 1-2 moles of an amine containing from 1 to 5 nitrogens and from 2 to 20 carbons and 1 molar equivalent of a source of molybdenum of the class consisting of molybdic trioxide, ammonium thiomolybdate, ammonium bismolybdate molybdenum halides and ammonium tetrahydrate, the improvement of using from 0.25 to 5 parts by weight of an alkyl substituted phenol wherein said alkyl group contains from 5 to 50 carbons for said reaction solvent which is carried out at a temperature of from 135° C. to 225° C. whereby a more readily filterable reaction product is obtained.

2. A concentrate according to claim 1 wherein said alkyl substituent contains from 8 to 18 carbons, said temperature is from 160° C. to 190° C. and carried out over a period of from 4 to 20 hours.

3. A concentrate according to claim 1 wherein said complex is obtained as the solution reaction product of a hydrocarbyl substituted thio-bis-phenol reacted with about 0.5 molar equivalent of a molybdenum source of the class consisting of molybdic trioxide, ammonium thiomolybdate, ammonium bis-molybdate, molybdenum halides and ammonium heptamolybdate and one mole of an amine selected from the class of $C_6$-$C_{30}$ alkylamine, alkylene polyamines and their ethoxylated derivatives, alkanolamines urea and ureides and dissolved in from 0.25 to 5 parts by weight of a $C_5$-$C_{50}$ alkyl substituted phenol solvent per part by weight of said product.

4. A concentrate according to claim 2 wherein said thio-bis-phenol is nonyl phenol sulfide, said molybdenum source is molybdic trioxide, said amine is ethylenediamine and said phenol solvent is nonyl phenol present in an amount of about 1 part by weight.

5. A concentrate according to claim 2 diluted with mineral oil in an amount of up to about the weight of said phenol solvent.

6. A concentrate according to claim 2 wherein said phenol is a $C_8$-$C_{10}$ alkyl substituted phenol.

7. A concentrate according to claim 1 wherein said complex is obtained as the product of a hydrocarbyl substituted thio-bis-phenol reacted with about 0.5 molar equivalent of molybdic trioxide and one mole of an amine selected from the class of $C_6$-$C_{30}$ alkylamine, alkylene polyamines and their ethoxylated derivatives, alkanolamine, urea and ureides and dissolved in from 0.25 to 5 parts by weight of a $C_5$-$C_{50}$ alkyl substituted phenol solvent per part by weight of said product.

8. A hydrocarbon composition comprising a major portion of a hydrocarbon and at least a friction reducing amount of the combination of: (a) an organo molybdenum complex obtained from an alkanol solution reaction of 1-2 moles of a $C_1$ to $C_{50}$ hydrocarbyl substituted thio-bis-phenol, 1-2 moles of an amine reactant containing from 1 to 5 nitrogens and from 2 to 20 carbons and 1 molar equivalent of a source of molybdenum of the class consisting of molybdic trioxide, ammonium thiomolybdate, ammonium bismolybdate, molybdenum halides and ammonium tetrahydrate; (b) an oil-soluble active sulfur donor; and from 0.25 to 5 parts by weight of a $C_5$-$C_{50}$ alkyl substituted phenol per part by weight of said complex, said combination providing from about 0.005 to 0.2 weight percent molybdenum and said sulfur donor being present in at least 0.25 weight percent, all of said weight percent being based on the total weight of said composition.

9. A hydrocarbon composition according to claim 8 wherein said hydrocarbon is mineral oil, said organo complex is an oil-soluble reaction product of a hydrocarbyl substituted thio-bis-phenol with about 0.5 molar equivalent of a molybdenum source of the class consisting of ammonium thiomolybdate, molybdic anhydride, ammonium bismolybdate, molybdenum halides and ammonium heptamolybdate tetrahydrate and one mole of ethylene diamine, said sulfur donor is an oil-soluble dihydrocarbyl ester of dithiophosphoric acid and the alkyl group of said phenol contains 8 to 18 carbons.

10. A hydrocarbon composition according to claim 9 wherein said mineral oil has a viscosity as measured by ASTM D-445 of about from 2-40 centistokes at 99° C., said thio-bis-phenol is nonyl phenol sulfide, said molybdenum source is molybdic trioxide, said active sulfur donor is zinc dihydrocarbyl dithiophosphate present in an amount of from 0.2-2 parts by weight per part by weight of molybdenum complex and said phenol is nonyl phenol.

11. A hydrocarbon composition according to claim 8 wherein said hydrocarbon is mineral oil, said organo complex is an oil-soluble reaction product of a hydrocarbyl substituted thio-bis-phenol with about 0.5 molar equivalent of molybdic trioxide and one mole of ethylene diamine, said sulfur donor is an oil-soluble dihydrocarbyl ester of dithiophosphoric acid and the alkyl substituent of said phenol contains 8 to 10 carbons.

12. A method of preparing an organo molybdenum complex containing from about 0.5 to 5 wt.% nitrogen comprising the steps of reacting a $C_1$ to $C_{50}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides and ammonium heptamolybdate tetrahydrate and one mole of an amine containing from 1 to 5 nitrogens and from 2 to 20 carbons, while dissolved in from to 5 parts by weight of an $C_5$-$C_{50}$ alkyl substituted phenol solvent per part by weight of said product at a temperature of from about 145° C. to 225° C. for about 4 to 20 hours.

13. The method of claim 12 wherein said time of reaction is from 6 to 12 hours and at a temperature of about 160° C. to 190° C.

14. The method of claim 13 wherein said thio-bis-phenol is nonyl phenol sulfide, said alkyl phenol is nonyl phenol and said amine is ethylene diamine.

15. A gasoline composition comprising gasoline containing from 10 to 1,000 parts per million based on the total weight of the gasoline composition of a molybdenum complex-phenol solution obtained from an alkyl phenol solution reaction of a $C_1$ to $C_{50}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides, and ammonium heptamolybdate tetrahydrate and one mole of an amine containing from 1 to 5 nitrogens and from 2 to 20 carbons while dissolved in from 0.25 to 5 parts by weight of a $C_5$–$C_{50}$ alkyl substituted phenol solvent per part by weight of said complex.

* * * * *